United States Patent
Kennedy, II (10) Patent No.: US 8,100,903 B2
(45) Date of Patent: Jan. 24, 2012

(54) SPHINCTEROTOME IMPROVEMENT

(75) Inventor: Kenneth C. Kennedy, II, Clemmons, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 678 days.

(21) Appl. No.: 11/284,528

(22) Filed: Nov. 21, 2005

(65) Prior Publication Data

US 2006/0161188 A1 Jul. 20, 2006

Related U.S. Application Data

(60) Provisional application No. 60/630,887, filed on Nov. 24, 2004.

(51) Int. Cl.
A61B 18/18 (2006.01)

(52) U.S. Cl. .......................................... 606/47

(58) Field of Classification Search ................ 606/47, 606/170, 110, 113, 167
See application file for complete search history.

(56) References Cited

U.S. PATENT DOCUMENTS

| | | | | |
|---|---|---|---|---|
| 3,739,784 A | * | 6/1973 | Itoh | 606/113 |
| 3,903,892 A | * | 9/1975 | Komiya | 606/110 |
| 4,325,374 A | * | 4/1982 | Komiya | 606/47 |
| 5,075,062 A | * | 12/1991 | Karpiel | 264/171.2 |
| 5,971,994 A | * | 10/1999 | Fritzsch | 606/113 |
| 5,984,920 A | * | 11/1999 | Steinbach | 606/47 |
| 6,193,729 B1 | * | 2/2001 | Holsinger | 606/113 |
| 6,352,539 B1 | * | 3/2002 | Avellanet | 606/113 |
| 6,491,680 B1 | * | 12/2002 | Batiste | 604/523 |
| 6,652,551 B1 | * | 11/2003 | Heiss | 606/170 |
| 6,827,718 B2 | * | 12/2004 | Hutchins et al. | 606/47 |
| 2002/0072745 A1 | * | 6/2002 | Truckai et al. | 606/47 |
| 2003/0060842 A1 | | 3/2003 | Chin et al. | |
| 2005/0209590 A1 | * | 9/2005 | Terakura | 606/47 |
| 2007/0118112 A1 | * | 5/2007 | Kennedy, II | 606/45 |
| 2008/0009884 A1 | * | 1/2008 | Kennedy, II | 606/127 |

FOREIGN PATENT DOCUMENTS

EP  0 385 588  9/1990
JP  2002-102242  4/2002

OTHER PUBLICATIONS

Japanese Office Action for Patent Application No. JP 2007-543470 including an English translation, 5 pgs.

* cited by examiner

*Primary Examiner* — Ryan Severson
*Assistant Examiner* — Sarah Simpson
(74) *Attorney, Agent, or Firm* — Brinks Hofer Gilson & Lione (57) ABSTRACT

A sphincterotome comprising a tensioning mechanism to adjust relative tension between a filament and shaft thereof. In one embodiment, the tensioning mechanism adjusts relative tension and or length at a connection of the sphincterotome handle assembly to one or both of the shaft and filament. In another embodiment, the tensioning mechanism adjusts relative tension and or length where it is disposed along the filament.

23 Claims, 9 Drawing Sheets

A) Pull Force 0 to 0.2 lbf

FIG. 6B

B) Pull Force 0.225 lbf

FIG. 6C

C) Pull Force 0.25 lbf — Handle & Spring Cover in Contact

FIG. 6D

D) Pull Force 0.5 lbf — Handle & Spring Cover in Contact

FIG. 7

SPHINCTEROTOME IMPROVEMENT

BACKGROUND OF THE INVENTION

The present device relates to medical devices, and specifically to improvements to devices such as sphincterotomes, also known as papillotomes.

In endoscopic, or other minimally invasive surgery, generically referred to herein as endoscopic surgery, a sphincterotome may be used in conjunction with an endoscope to provide surgical cutting inside a patient. Specifically, a sphincterotome is used during certain procedures to make an incision in a sphincter. For example, a common treatment of cholecystitis includes the removal of gallstones from the common bile duct. This is frequently done endoscopically with the use of a duodenoscope. The common bile duct proceeds from the junction of the common hepatic duct with the cystic duct, which is open to the gall bladder, and merges with the pancreatic duct, forming the ampulla of Vater, which itself opens into the duodenum at the papilla of Vater. The sphincter of Oddi is a muscular ring that controls passage of fluid from the ampulla of Vater into the duodenum. For removal of gallstones in an endoscopic procedure, access to the common bile duct for removal of gallstones is eased using a sphincterotome to incise or sever the sphincter of Oddi. The sphincterotome is introduced through the duodenoscope and guided through the duodenum to the common bile duct. Once the sphincterotome is guided into the sphincter, its cutting element, commonly a needle knife or cutting wire, is used to incise the sphincter, and thereby improve access to the bile duct and impacted gallstones.

Another example of a common procedure utilizing a sphincterotome is endoscopic retrograde cholangiopancreatography (ERCP), a diagnostic visualization technique used for variety of clinical applications. In this procedure, a contrast fluid such as a radio-opaque dye is introduced through a tube into the ampulla of Vater. A sphincterotome is often employed to provide access through the sphincter of Oddi in the same manner as described above. ERCP is often used in diagnosis of cholecystitis, as well as in the diagnosis and treatment of other conditions of the pancreatic and common bile ducts and related structures.

Figure 1:
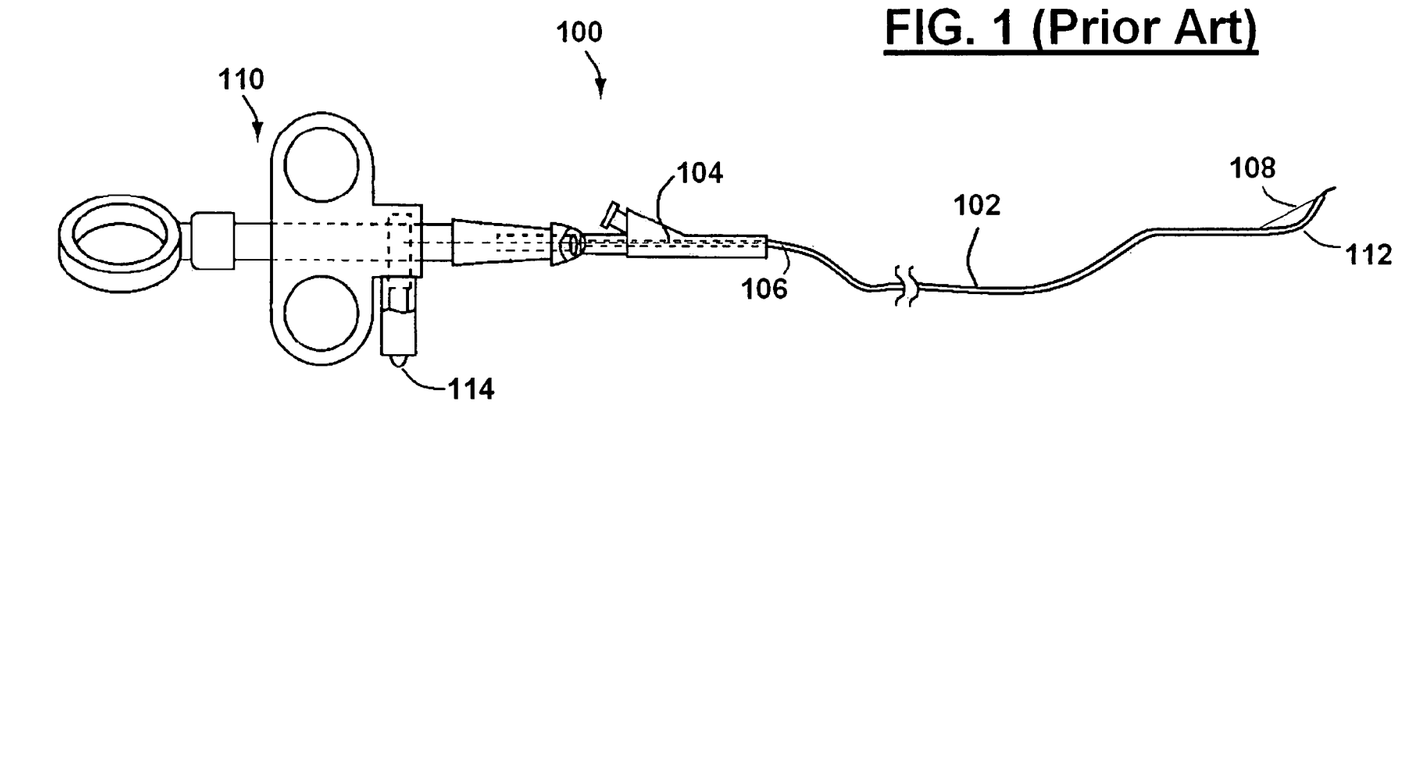
FIG. 1 is a typical prior art sphincterotome.

As illustrated in FIG. 1, a typical prior art sphincterotome 100 includes a polymer tubular shaft 102 made of PTFE (polytetrafluoroethylene) or another flexible material. An electroconductive filament 104, also called a drive wire, is disposed in a lumen 106 running through the shaft 102. The distal end of the filament 104 is connected or anchored to the distal end of the shaft 102. A short segment of the electroconductive filament 104 near the distal end thereof is disposed outside of the shaft 102 for use as an electrocautery cutting wire 108. The proximal end of filament 104 is connected to the proximal handle assembly 110 such that actuation of the handle assembly 110 partially retracts (i.e., pulls in a proximal direction) the filament 104 relative to the polymer shaft 102. This actuation results in the distal end of shaft 102 bowing to form an arc 112, with the exposed filament forming a secant of the arc 112 so as to form a cutting wire 108. Electric current passed through the filament 104 from an electrode 114 in the handle assembly 110 enables the cutting wire 108 to act as an electrosurgical cutting element that may be used effectively to cut and cauterize tissue, such as the sphincter of Oddi in the example procedures described above.

One problem that often arises during or as the result of manufacture of this type of sphincterotome 100 is over-tensioning or under-tensioning of the electroconductive filament 104 relative to the shaft 102 due to length changes of the shaft 102 or filament 104 that may occur after the 104 filament is assembled to the sphincterotome 100. For example, the polymer tube 102 may shrink or elongate as a result of curing or some other post-assembly process (e.g., heating and/or sterilization). However, the electroconductive filament 104 will rarely undergo an identical shrinkage or elongation due to its different composition. As a result, and because the filament 104 and the shaft 102 are fixedly connected at the proximal and distal ends, any change in relative length between the filament 104 and the shaft 102 will generate compressive or tensile forces in these structures. The compressive or tensile forces in the filament 104 and the shaft 102 may interfere with the function of the sphincterotome. For example, if the shaft 102 elongates relative to the filament 104, then the shaft 102 will undergo compression, and the filament 104 will undergo tension (i.e., over-tensioning) which results in bowing of the shaft 102 prior to actuation in surgical use. On the other hand, if the shaft 102 shrinks in length relative to the filament 104, the resulting decrease of relative tension in the filament 104 (i.e., under-tensioning or bagginess) may cause a slackness in the filament 104 that can interfere with the proper actuation of the sphincterotome 100 during surgical use. The present invention provides a mechanism for adjusting the tension in the sphincterotome filament and/or compression in the shaft to alleviate both problems of over-tensioning and under-tensioning.

BRIEF SUMMARY OF THE INVENTION

In one aspect, the present invention includes a sphincterotome, having a handle assembly connected to a flexible elongate shaft that includes a first lumen, a proximal end, and a distal end. The sphincterotome includes an electroconductive filament with a proximal section and a distal section, the proximal section having a proximal attachment to the handle assembly, and the distal section having a distal attachment near the distal end of the shaft. At least a portion of the proximal section of the filament is disposed through at least a portion of the first lumen, and at least a portion of the distal section of the filament is disposed outside the shaft for use as a cutting element. The proximal attachment includes a tensioning mechanism for adjusting at least one of a tension in the filament and a compression in the shaft.

In another aspect, the present invention includes a sphincterotome having an elongate shaft; a first handle portion comprising an attachment to the shaft; and a second handle portion mounted to the first handle portion in a manner allowing proximal and distal sliding movement of the second handle portion relative to the first handle portion. The second handle portion includes an attachment to an electroconductive filament, which is connected at its distal end to a distal end of the shaft. A portion of the filament extends through a portion of a lumen of the shaft such that when the second handle portion is moved in a proximal direction relative to a first handle portion, the filament is pulled in the proximal direction relative to the lumen of the shaft. At least one of the first handle portion and the second handle portion includes a tensioning mechanism for adjusting at least one of a tension in the filament and a compression in the shaft.

In yet another aspect, the present invention includes a sphincterotome having a first handle portion with a connection to an elongate shaft and a second handle portion mounted to the first handle portion in a manner allowing proximal and distal sliding movement of the second handle portion relative to the first handle portion. The second handle portion includes a connection to a filament and a tensioning mechanism for adjusting a tension of the filament. The tensioning mechanism is connected to the filament such that during a first stage of movement, the movement of the second handle portion relative to the first handle portion equals a first distance, and the movement of the filament relative to the shaft equals a second distance, wherein the first distance is greater than the second distance. During a second stage of movement, the movement of the second handle portion relative to the first handle portion equals a third distance, and the movement of the filament relative to the shaft equals a fourth distance, wherein the third distance is substantially equal to the fourth distance.

In still another aspect, the present invention includes a sphincterotome with a tubular shaft having a shaft length, a proximal end portion and a distal end portion. The sphincterotome also includes a filament having a filament length, a proximal end portion and a distal end portion. The distal end portion of the filament is affixed to the distal end portion of the shaft. The sphincterotome has a first handle component comprising an attachment to the proximal end portion of the filament and a second handle component reciprocally attached to the first handle component, the second handle component comprising an attachment to the shaft. At least one of the attachment of the first handle component to the filament and the attachment of the second handle component to the shaft is adjustable.

In yet another aspect, the present invention includes a sphincterotome having an elongate shaft; a first handle portion with an attachment to the shaft; and a second handle portion mounted to the first handle portion in a manner allowing proximal and distal sliding movement of the second handle portion relative to the first handle portion. The second handle portion includes an attachment to an electroconductive filament, which is connected at its distal end to a distal end of the shaft. A portion of the filament extends through a portion of a lumen of the shaft such that when the second handle portion is moved in a proximal direction relative to a first handle portion, the filament is pulled in the proximal direction relative to the lumen of the shaft. One of the shaft and the filament includes a tensioning mechanism for adjusting at least one of a tension in the filament and a compression in the shaft.

DETAILED DESCRIPTION

The following disclosure describes embodiments of a sphincterotome having a handle assembly comprising a tension-adjusting mechanism for adjusting the tension of the electroconductive filament/cutting wire relative to the sphincterotome shaft. Those of skill in the art will appreciate that variations of the described embodiments as well as other embodiments are possible and within the scope of this application.

Figure 2:
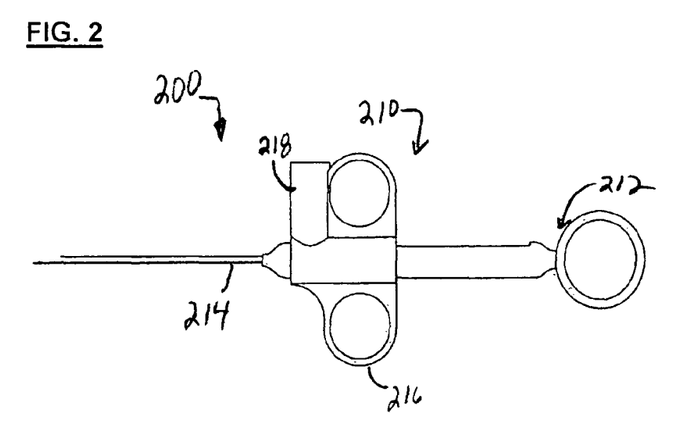
FIG. 2 is an external side view of an embodiment of a handle of the present invention.

FIGS. 2-4A, 5, and 6A-6E illustrate one embodiment of a handle assembly 210 of a sphincterotome 200. FIG. 2 shows a side external view of the handle assembly 210, which is commonly referred to as a three-ring handle. The handle assembly 210 comprises a first portion and a second portion. In the illustrated embodiment, the first portion is a one-ring (commonly referred to as a thumb ring or stem) handle component 212 that is attached to the proximal end of the tubular catheter shaft 214 of the sphincterotome 200. The second portion is a two-ring (commonly referred to as a finger ring or spool) handle component 216 that is slidably mounted to the one-ring handle component 212. As is explained in greater detail below, the two-ring handle component 216 is connected to an electroconductive filament 224. The two-ring handle component 216 also includes a housing 218 for supporting an electrode 220. Persons of skill in the art will appreciate that many other embodiments of a sphincterotome handle are possible and practicable. For example, the handle assembly may use a different number of rings, a trigger grip, or other gripping surfaces adapted for manipulating a sphincterotome. As another example, the connection between handle components and the shaft and filament may be reversed. Other structures such as a utility port for access to a lumen in the sphincterotome shaft may also be located on a first or second portion of a handle assembly.

Figure 3:
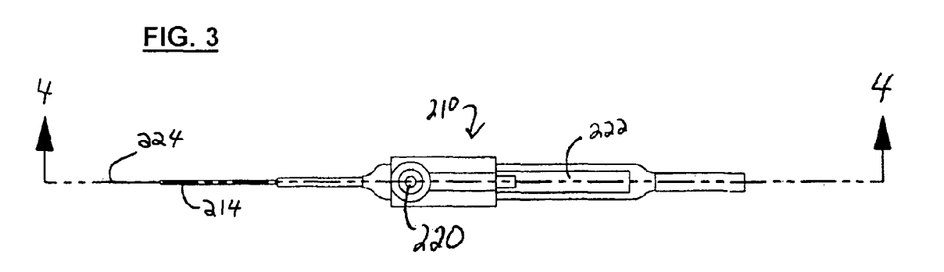
FIG. 3 is a top view of a handle of the present invention.
Figure 4:
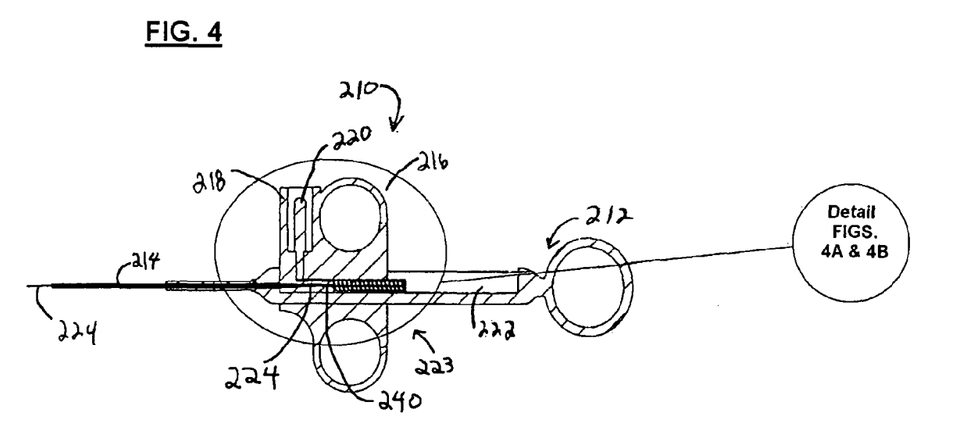
FIG. 4 is a side view of a longitudinal cross-section of a handle of the present invention.
Figure 5:
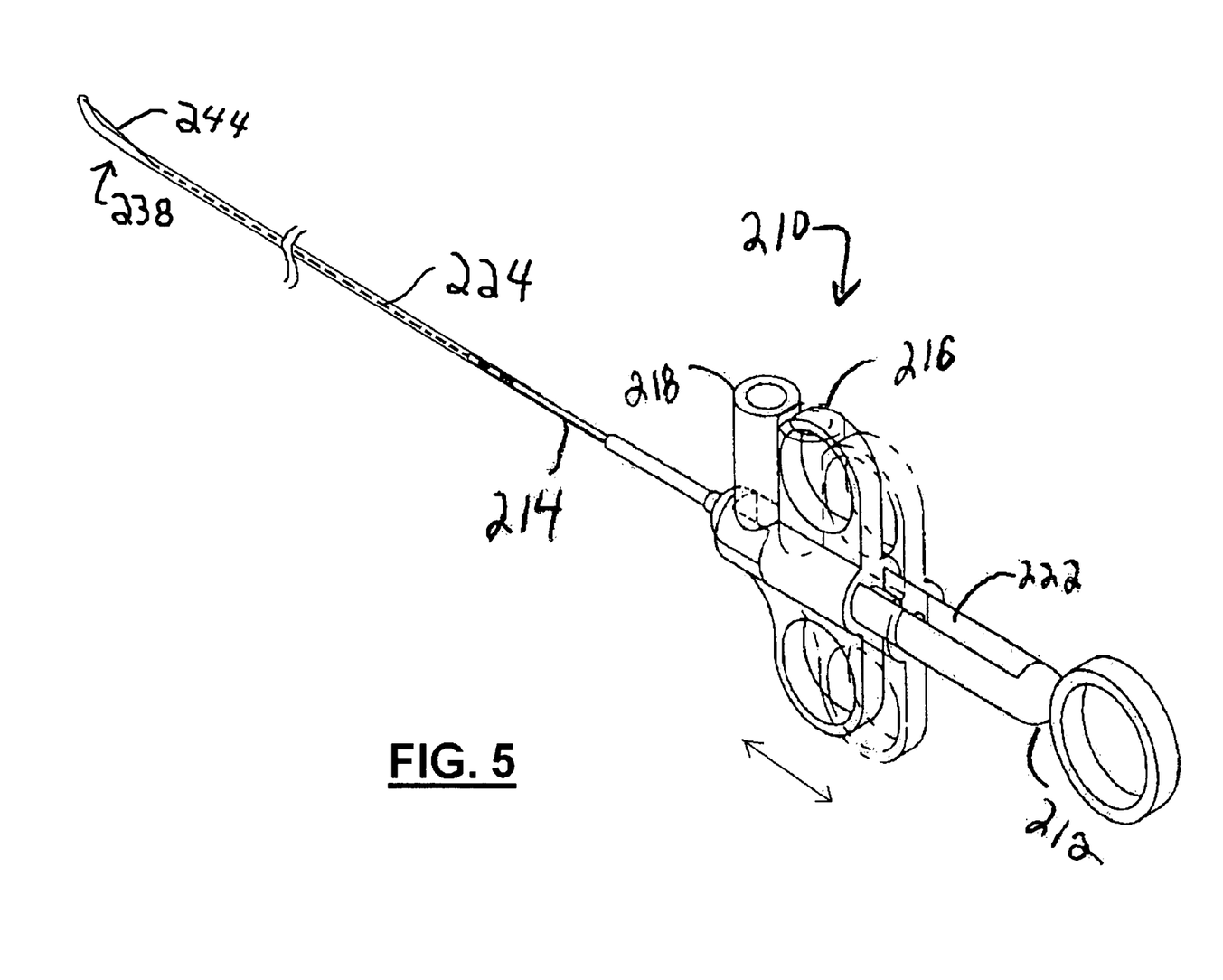
FIG. 5 is a perspective view of a handle of the present invention, showing motion thereof.

FIG. 3 illustrates a top view of the handle assembly 210, and FIG. 4 illustrates a longitudinal cross-sectional view of the handle assembly 210 taken along line 4-4 of FIG. 3. As can be seen in these figures, the one-ring handle component 212 has a channel 222 extending along the length thereof. The channel 222 is slidingly occupied by a portion of the two-ring handle component 216. As is illustrated in FIG. 5, the two-ring handle component 216 is slidingly movable along a proximal-distal axis relative to the one-ring handle component 212. As will be appreciated by those skilled in the art, two or more handle portions of a sphincterotome may be constructed to move relative to each other in different ways (e.g., a rotary action).

The portion of the two-ring handle component 216 which is slidingly disposed in the channel 222, together with the channel 222, houses a tensioning mechanism 223 for adjusting the tension in the electroconductive filament 224 and/or the compression in the shaft 214. The distal portion of the two-ring handle component 216 that is in the channel 222 also includes a filament channel 240 through which the filament 224 is slidingly disposed. The tensioning mechanism 223 is more clearly illustrated in FIG. 4A, which is an enlarged detail of the central portion of the handle assembly shown in FIG. 4.

Figure 4A:
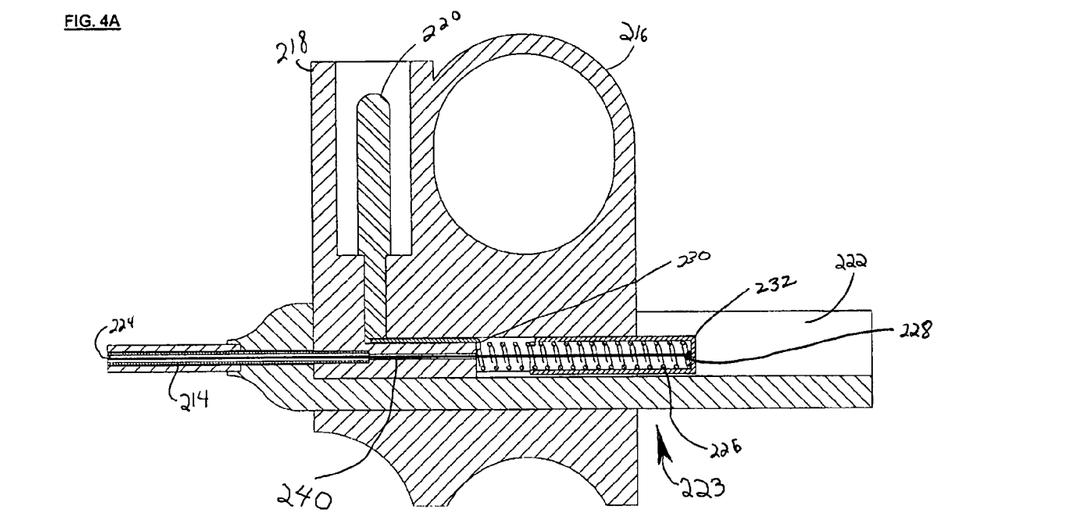
FIG. 4A is a detail of FIG. 4.

In the tensioning mechanism 223, the spring 226 is partially compressed during assembly of the handle 210 so that it provides a low, latent tension in the filament 224. If the shaft 214 lengthens or shrinks relative to the filament 224 following assembly, the spring 226 compresses or relaxes so as to absorb change in relative tension of the filament 224 and/or compression in the shaft 214. In the embodiment illustrated, the spring 226 is compressed to the middle of its total travel during initial assembly. In this embodiment, the axial compliance of the spring 226 is significantly greater than the distal bowing compliance of the shaft 214 (relative compliance of 10:1, such that a 1 unit compression of the spring results in only about a 0.1 unit relative bowing of the distal end of the shaft 214).

For example, the sphincterotome shaft may lengthen after assembly as a result of curing or sterilization of the shaft material. As noted in the background section above, if this happens in the typical prior art sphincterotome, then the filament will become over-tensioned, causing premature bowing of the sphincterotome's distal end. In contrast, if the sphincterotome shaft 214 of the present invention lengthens after assembly, the spring 226 will compress, thereby absorbing the longitudinal tension created in the filament 224 by the lengthening of the shaft 214. Likewise, in typical prior art sphincterotomes, if the shaft shrinks following assembly, the filament will slacken, which may impair proper functioning of the device. However, in the present invention, if the sphincterotome shaft 214 shrinks after assembly, then the spring 226 will relax/expand, thereby maintaining a minimum tension in the filament 224. The tensioning mechanism of the present invention will likewise adjust the tension in the filament 224 as a result of changes in the length of the filament 224 as opposed to that of the shaft 214.

In the embodiment illustrated in FIGS. 2-4A, 5, and 6A-6E, a lead 230 connects the spring 226 to an electrode 220. When the sphincterotome 200 is connected to an activated electrosurgical generator, the current from the generator will travel via the electrode 220 through the lead 230, the spring 226, and the filament 224. An insulative plastic cover 232 affixed to the proximal end of the spring 226 and the proximal end 228 of the filament 224 is provided to shield the portion of the filament 224 and spring 226 that are exposed in the channel 222. The cover 232 has at least two functions: (1) it prevents a conductive surface from being exposed in the channel 222 where a person operating the sphincterotome could inadvertently sustain an electric shock by touching the exposed conductive surface, and (2) as will be shown in greater detail below, the distal end of the cover 232 serves as a contact point with a proximal surface 231 of the two-ring handle component 216 for translating force from the two-ring handle component 216 to the filament 224. In alternative embodiments, the spring 226 may be constructed from a non-conductive material, and the electrode 220 may be connected to the filament 224 via a different path.

Many variations of the presently illustrated embodiment are possible that will provide the desired tensioning of the filament 224 and a path for electric current thereto. For example, the proximal end of the filament 224 could itself be configured as a coil spring or other shape suitable for tension adjustment. In other alternative embodiments, rather than a coil spring, the tensioning mechanism may include a leaf spring, a limited flex tang, or some other structure for controlling tension.

Figure 6A:
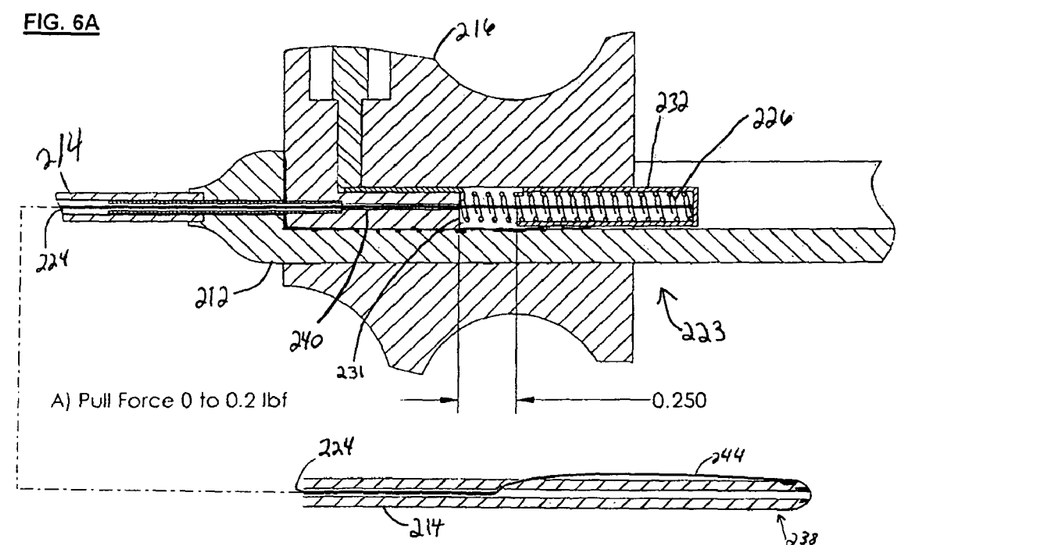
FIGS. 6A-6E each show a side view of a longitudinal cross-section of a handle of the present invention at different stages of movement/actuation.
Figure 6B:
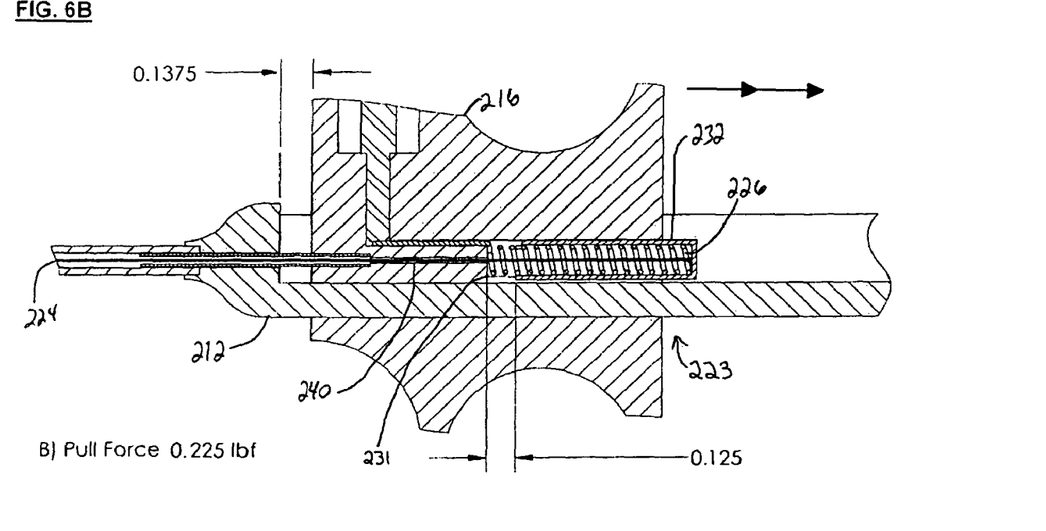
Figure 6C:
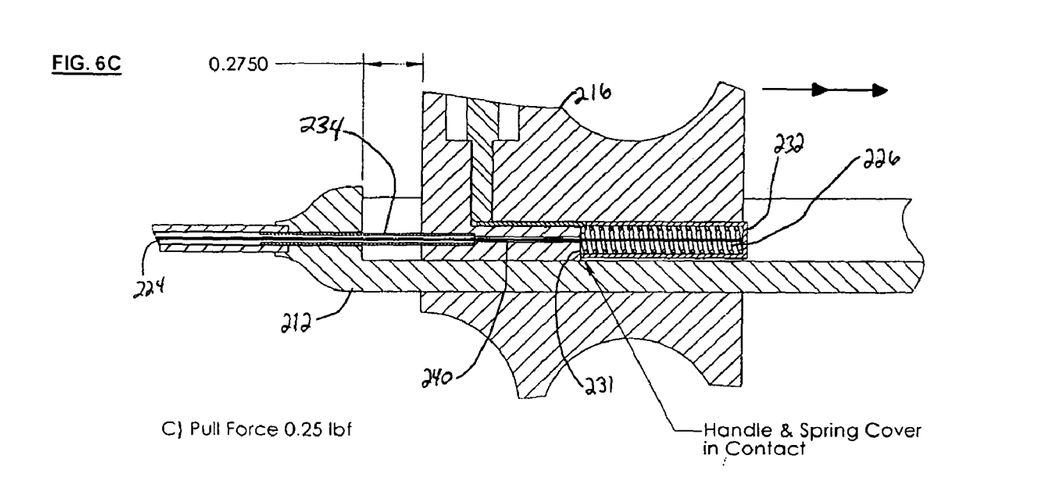
Figure 6D:
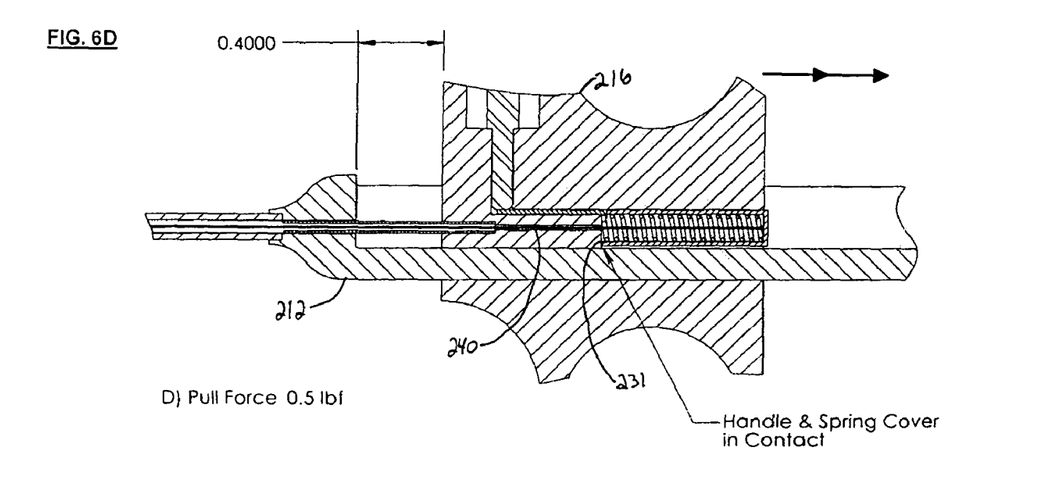
Figure 6E:
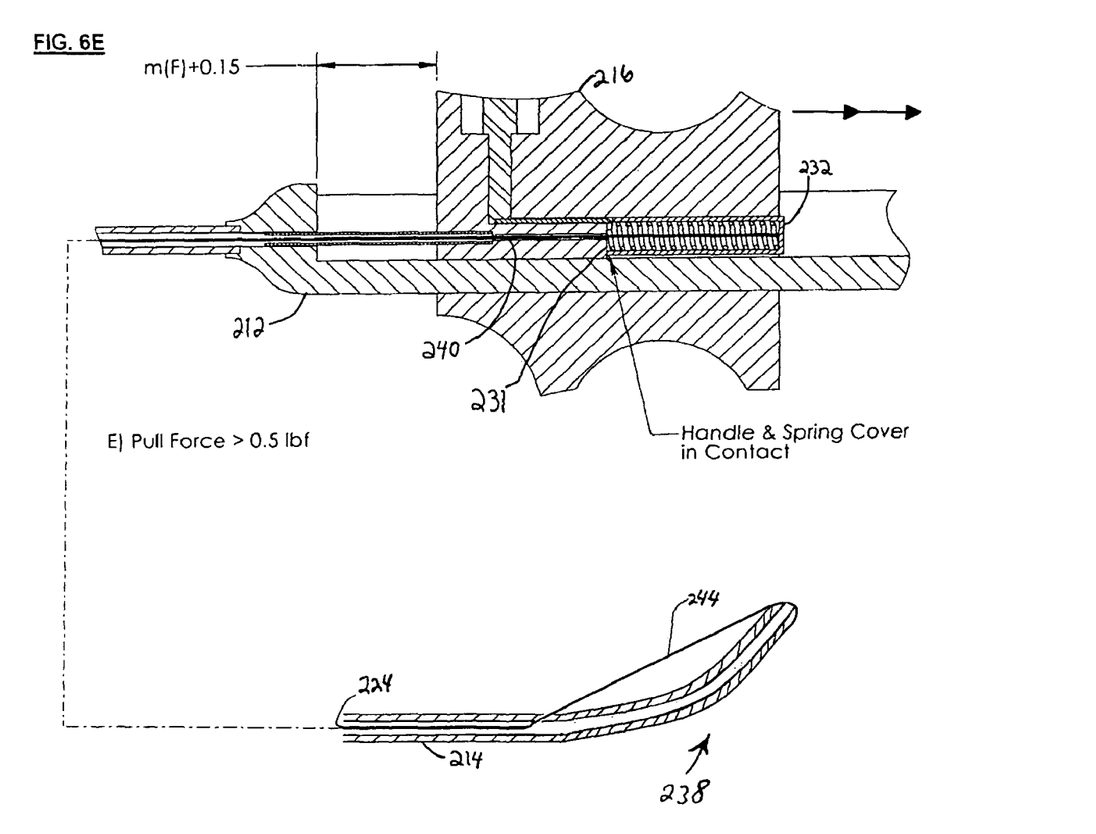
Figure 7:
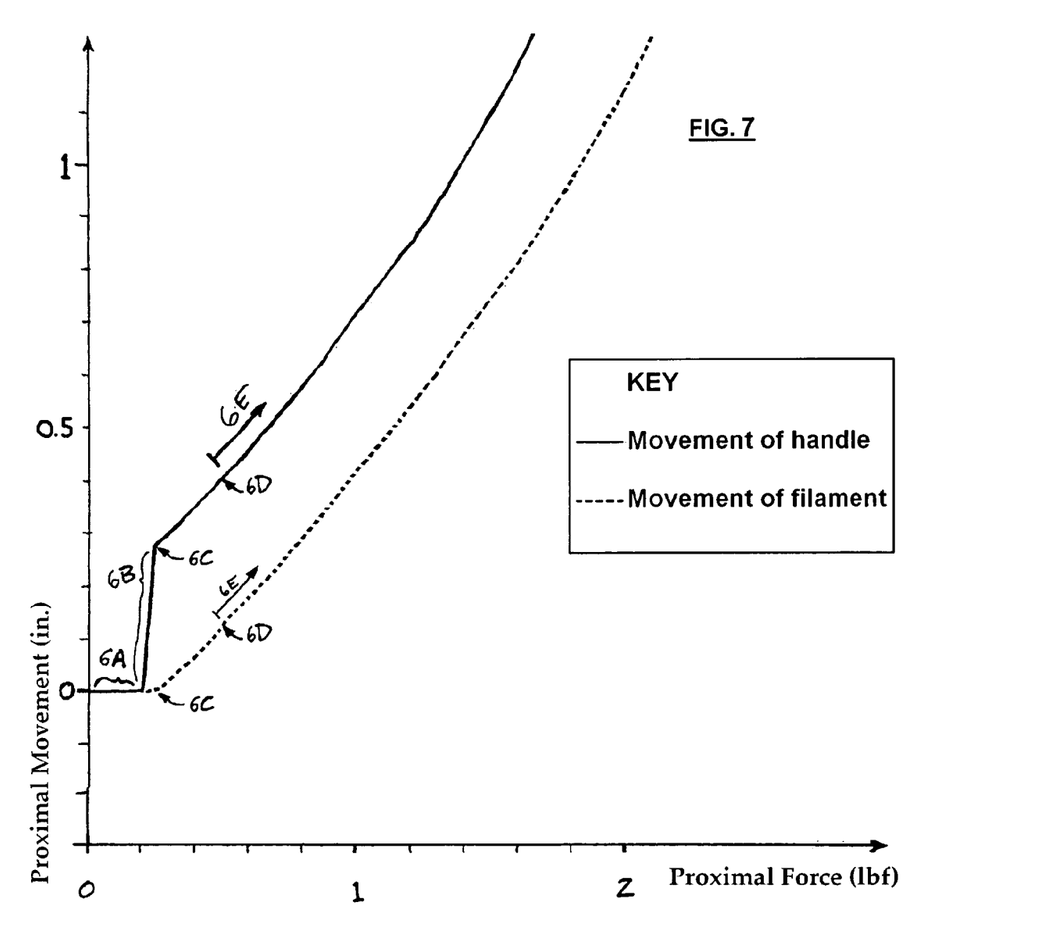
FIG. 7 is a graph illustrating the present invention at the different stages of movement/actuation shown in FIGS. 6A-6E.

FIGS. 6A-6E and FIG. 7 illustrate how the above-described tensioning mechanism 223 operates during actuation of the handle assembly 210 for actuation of the sphincterotome (i.e., actuating the handle assembly 210 to intentionally tension the filament 224 so that its distal cutting portion 244 is actuated/bowed for cutting). Specifically, FIGS. 6A-6E show pictorially the effect on the spring 226 and the filament 224 of applying proximally directed force to advance the two-ring handle component 216 relative to the one-ring handle component 212. FIG. 7 summarizes in graphic form the effect upon movement of two-ring handle component 216 (relative to the movement of the filament 224) of exerting force on the two-ring handle component 216. In FIG. 7, the stages of movement of the two-ring handle component 216, as illustrated in FIGS. 6A-6E, are indicated by reference to each of FIGS. 6A-6E. The graph is plotted with the proximal longitudinal movement of the two-ring handle component 216 and the filament 224 (in inches) shown on the Y-axis and the proximally directed force (in pounds-force (lbf)) exerted on the two-ring handle component 216 shown on the X-axis.

FIG. 6A illustrates an enlarged cross-sectional view of the tensioning mechanism "at rest" (with the spring pre-loaded). The filament 224 is movably disposed through a filament channel 240 of the two-ring handle component 216. In the illustrated embodiment, when the proximal pulling force (on the two-ring handle component 216) is 0 to 0.2 lbf, there is a 0.25 inch gap between the surface 231 at the proximal end of the filament channel 240 and the spring cover 232. The spring 226 exerts an initial tension (of 0-0.2 lbf) on the filament 224 as the result of the spring 226 being partially compressed during initial assembly as discussed above, and should still be partially compressed even if post-assembly changes in the length of the shaft 214 and/or the filament 224 have occurred. As a result, this initial tension should not result in substantial bowing of the distal end 238 of the shaft 214. As a result, the distal section 244 of the filament 224 that is disposed outside of the shaft 214 is not in an actuated position for use as a cutting element. The position of the filament 224 relative to the shaft 214 consequently will not interfere with advancement of the sphincterotome through a working channel of an endoscope. FIG. 6A also illustrates that the initial proximal pulling force must exceed 0.2 lbf to overcome static frictional forces inherent in the handle (i.e., less than 0.2 lbf force will not move the handle significantly). This is clearly illustrated in the graph in FIG. 7.

As shown in FIG. 6B, when the proximal pull force is increased to 0.225 lbf, the proximal pull force overcomes static frictional forces inherent in the handle and advances the two-ring handle component 216 proximally by 0.1375 inches. The spring 226 partially compresses and, together with the cover 232 (which is attached to the proximal end of the spring 226 and filament 224) moves a short distance proximally leaving a 0.125 inch gap between the proximal end surface 231 of the filament channel 240 and the distal end of the spring cover 232. It should be appreciated that the degree of proximal movement of the spring 226 and the spring cover 232, relative to that of the two-ring handle component 216, is a function of the spring constant of the spring 226 relative to the stiffness of the distal end 238 of the shaft 214. Most of the initial movement of the two-ring handle component 216 is consumed by the spring 226, and the filament 224 does not move any significant distance.

As shown in FIG. 6C, a pull force to 0.25 lbf advances the two-ring handle component 216 by 0.275 inches, placing the proximal end surface 231 of the filament channel 240 and the spring cover 232 in contact with each other. This movement increases the tension on the filament 224, but does not move the filament 224 a significant distance. FIG. 6C also illustrates an insulative wrap 234 for the portion of the filament 224 that is exposed in the channel 222 as the two-ring handle component 216 is advanced proximally. As embodied here, this wrap 234 is slidable relative to the one-ring handle component 212 and relative to the shaft 214. As shown in FIGS. 6C-6D, the spring 226 is sufficiently compressed so that there is contact between the proximal end surface 231 of the filament channel 240 and the distal end of the spring cover 232. As a result, further proximal advancement by application of proximally directed force on the two-ring handle component 216 results in the translation of that force via the surface 231, through the cover 232, and consequently to the filament 224. This illustration is continued in FIGS. 6D-6E as a proximally directed force of 0.5 lbf and greater is exerted. The graph of FIG. 7 illustrates how, once contact between the proximal end surface 231 of the filament channel 240 and the spring cover 232 is established, the proximal advancement of the two-ring handle component 216 directly (in about a 1:1 relationship) translates to proximal advancement of the filament 224. As shown in FIG. 6E, the force exerted is sufficient to actuate the distal end 238 of the sphincterotome shaft 214 by bowing it to expose the cutting portion 244 of the filament 224.

It should be appreciated that the measurements of movement and applied forces shown in FIGS. 6A-6E and FIG. 7 are merely exemplary of the embodiment illustrated herein and will be different in other embodiments depending upon the structural components of those embodiments. For example, a sphincterotome with a stiffer spring and a different sized handle assembly having first and second handle components would have a different relationship between the quantity of proximally exerted force on the first handle component and the distance that first handle component moves relative to the second handle component.

Figure 4B:
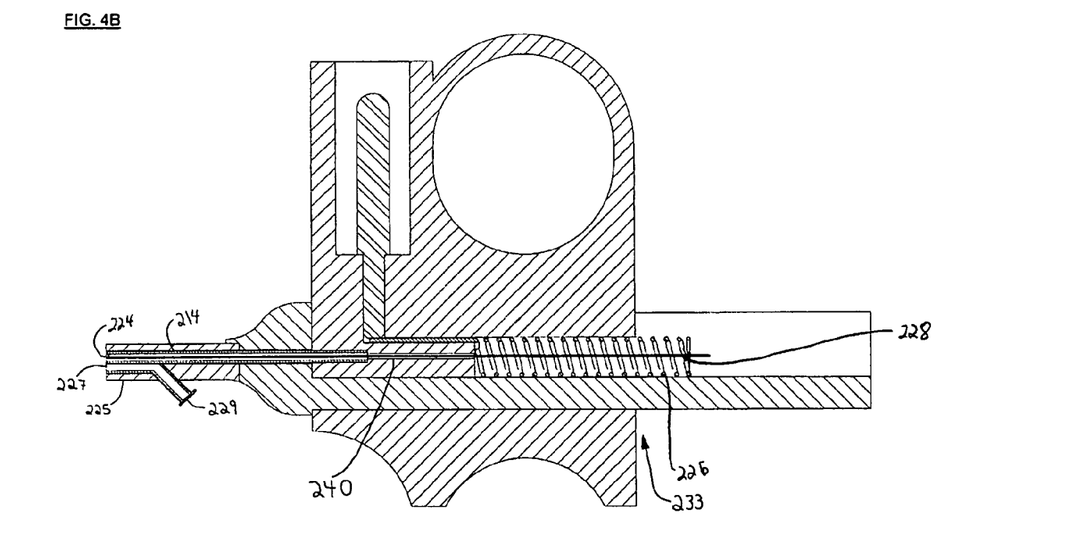
FIG. 4B is a detail side view of an alternative embodiment of a longitudinal cross-section of a handle of the present invention.

The present invention encompasses any tensioning mechanism that adjusts the length or compression of the shaft relative to the length or tension of the drive wire, and/or any tensioning mechanism that adjusts the attachment of the handle assembly to the shaft and/or filament. FIG. 4B illustrates an alternative embodiment of a tensioning mechanism using the same detail perspective as FIG. 4A. In the embodiment illustrated in FIG. 4B, a tensioning mechanism 233 includes an electroconductive coil spring 226 attached near its proximal end to near the proximal end 228 of the filament 224. The-attachment may be by, for example, welding or crimping. In this embodiment, bowing movement of the distal tip of the shaft (not shown) due to increased tension of the filament 224 by actuation of the handle assembly is limited while the spring 226 is being compressed. When the spring 226 is fully compressed (not shown), any further actuation of the handle assembly is translated directly into movement of the filament 224, which translates to movement of the filament's 224 distal attachment to the shaft 225 for bowing/actuation of the distal tip (not shown). As illustrated, this embodiment does not have a spring cover 232. Other embodiments may utilize a different type of spring cover or may, for example, have a portion of the spring coated with an insulative or other composition. Independent of the variant tensioning mechanism 233, this alternative embodiment also has a multi-lumen shaft 225 with a second lumen 227 open to a port 229, which may be used for injection of fluids such as contrast media.

Figure 8:
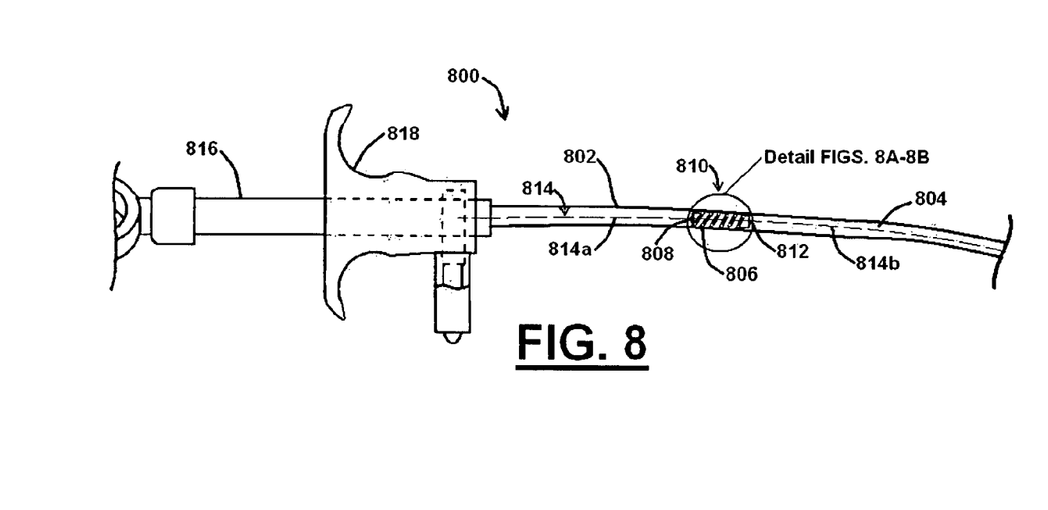
FIG. 8 is a side view of a sphincterotome embodiment of the present invention.
Figures 8A, 8B:
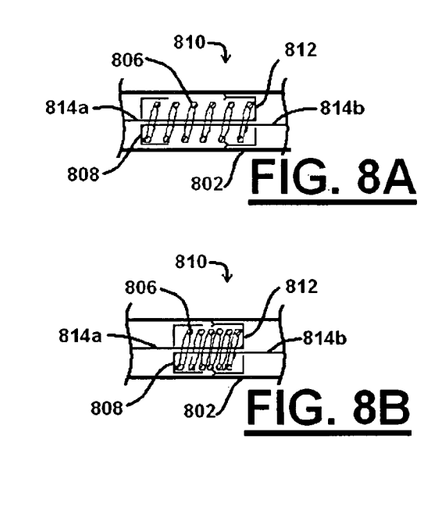
FIGS. 8A-8B each illustrate a detail view of FIG. 8.

FIGS. 8 and 8A-8B illustrate a sphincterotome embodiment wherein a tensioning mechanism 810 is included within the shaft 802 of a sphincterotome 800. FIG. 8 illustrates the sphincterotome 800. The sphincterotome has a first handle portion 816 attached to the shaft and a second handle portion 818 attached to the filament 814. FIGS. 8A-8B are detailed illustrations showing the tensioning mechanism 810 within the lumen 804 of the shaft 802. The tensioning mechanism 810 includes a spring 806 attached at its proximal end to a proximal end-cap 808 and at its distal end to a distal end-cap 812. The filament 814 has a proximal segment 814a and a separate distal segment 814b. The proximal filament segment 814a is attached to the distal end-cap 812, and the distal filament segment 814b is attached to the proximal end-cap 808.

The tensioning mechanism 810 is shown in an initial, partially compressed state in FIG. 8A. In this state, the spring 806 may expand if the shaft 802 expands relative to the filament 814. Or, as illustrated in FIG. 8B, the spring 806 may compress if the shaft 802 shrinks. FIG. 8B also indicates the function of the tensioning mechanism 810 when the sphincterotome handle portions 816, 818 are actuated to increase tension on the filament 814 for bowing the distal end (not shown) of the sphincterotome 800. Actuation of the handle portions 816, 818 increases the tension on the proximal filament segment 814a until the spring 806 is sufficiently compressed to bring the distal and proximal end-caps 812, 808 into contact with each other. At this contact point, the tensile force being exerted from the handle portions 816, 818 through the proximal filament segment 814a is translated substantially directly to the distal filament segment 814b.

In an alternative embodiment, the end-caps 808, 812 are not needed. In such an embodiment, the distal end of the proximal filament segment 814a is attached to the distal end of the spring 806 and the proximal end of the distal filament segment 814a is attached to the proximal end of the spring 806. In this arrangement, the point of substantially direct tension transmission from the proximal filament segment 814a to the distal filament segment 814b occurs when the spring 806 is fully compressed. In another alternative embodiment, the tensioning mechanism is mounted within a portion of the shaft to adjust the shaft's length (and tension/compression) relative to the filament.

Persons of skill in the art will appreciate that other arrangements of the tensioning mechanisms described herein are within the scope of the present invention. The materials and methods appropriate for use with the foregoing embodiments of the present invention but not explained in detail herein will be readily apparent to those skilled in the art. It is therefore intended that the foregoing detailed description be regarded as illustrative rather than limiting, and that it be understood that it is the following claims, including all equivalents, that are intended to define the spirit and scope of this invention.

I claim:
1. A sphincterotome, comprising:
a handle assembly;
a flexible elongate shaft connected to the handle assembly and comprising a first lumen, a proximal end, and a distal end;
an electroconductive filament comprising a proximal section and a distal section, the proximal section having a proximal attachment to the handle assembly, and the distal section having a distal end that is attached near the distal end of the shaft,
wherein at least a portion of the proximal section of the filament is disposed through at least a portion of the first lumen,
wherein at least a portion of the distal section of the filament is disposed outside the shaft for use as a cutting element;
wherein the proximal attachment comprises a generally longitudinally disposed tensioning spring mechanism that compensates between a generally longitudinal tension in the filament and a generally longitudinal compression in the shaft without an actuation of the electroconductive filament and without bowing the distal end of the flexible elongate shaft; and
wherein the tensioning spring mechanism is operatively connected to the proximal section of the filament such that the tensioning spring mechanism and the filament are moveable together without an actuation of the elec- troconductive filament and without bowing the distal end of the flexible elongate shaft.

2. The sphincterotome of claim 1, wherein the tensioning spring mechanism comprises a coil spring disposed generally longitudinally along a longitudinal axis of the sphincterotome, a first end of the coil spring being connected to a proximal end of the filament, and a second end of the coil spring being in contact with a surface of the handle assembly.

3. The sphincterotome of claim 2, wherein the second end of the coil spring is disposed against an interior surface of the handle assembly.

4. The sphincterotome of claim 2, wherein the tensioning spring mechanism further comprises a spring cover, the first end of the coil spring being disposed against the spring cover, and the proximal end of the filament being connected to the spring cover.

5. The sphincterotome of claim 4, wherein the first end of the coil spring is enclosed within an interior volume of the spring cover.

6. The sphincterotome of claim 1, configured such that an initial actuation movement of the handle assembly is translated to direct movement of the filament through the lumen of the shaft.

7. The sphincterotome of claim 1, configured such that an initial actuation movement of the handle assembly is substantially absorbed by the tensioning spring mechanism.

8. The sphincterotome of claim 7, configured such that a second actuation movement of greater magnitude than the initial actuation of the handle assembly is translated to direct movement of the filament through the lumen of the shaft.

9. The sphincterotome of claim 1, wherein the tensioning spring mechanism comprises a coil spring having a distal end and a proximal end, the proximal end of the coil spring being mounted adjacent a proximal end of the filament, the filament extending through a generally longitudinal interior of the coil spring.

10. The sphincterotome of claim 1, further comprising a longitudinal second lumen configured for passage of fluid therethrough.

11. The sphincterotome of claim 1, wherein the filament extends through the lumen from near the proximal end of the shaft to a location where the distal portion of the filament is disposed outside of the shaft for use as the cutting element, the cutting element being disposed near the distal end of the shaft.

12. The sphincterotome of claim 1, wherein the handle assembly comprises an electrode connection conductively connected to the filament.

13. The sphincterotome of claim 1, wherein the handle assembly comprises:
a first ring handle structure connected to the tubular shaft;
a second ring handle structure mounted to the first ring handle structure in a manner allowing proximal and distal sliding movement of the second ring handle structure relative to the first ring handle structure;
the second ring handle structure comprising the proximal attachment of the filament to the handle assembly;
configured such that proximal movement of the second ring handle structure relative to the first handle portion causes proximal movement of the filament relative to the lumen of the shaft; and
configured such that the tensioning spring mechanism is connected between the second ring handle structure and the filament.

14. The sphincterotome of claim 1, wherein the handle comprises:
a one-ring handle portion mounted to the tubular shaft;
a two-ring handle portion mounted to the one ring handle portion in a manner allowing proximal and distal sliding movement of the second handle portion relative to the first handle portion;
the two-ring handle portion comprising the proximal attachment of the filament to the handle assembly;
configured such that proximal movement of the two-ring handle portion relative to the one-ring handle portion causes proximal movement of the filament relative to the lumen of the shaft; and
wherein the tensioning spring mechanism is disposed in the two-ring handle portion.

15. A sphincterotome having a proximal end and a distal end, and comprising:
an elongate shaft;
a first handle portion comprising an attachment to the shaft; and
a second handle portion mounted to the first handle portion in a manner allowing proximal and distal sliding movement of the second handle portion relative to the first handle portion; the second handle portion comprising
an attachment to an electroconductive filament, the filament being connected at its distal end to a distal end of the shaft, a portion of the filament extending through a portion of a lumen of the shaft;
wherein, when the second handle portion is moved in a proximal direction relative to a first handle portion, the filament is pulled in the proximal direction relative to the lumen of the shaft;
at least one of the first handle portion and the second handle portion comprising a generally longitudinally disposed tensioning spring mechanism configured such that it compensates between a generally longitudinal tension in the filament and a generally longitudinal compression in the shaft without an actuation of the electroconductive filament and without bowing the distal end of the shaft; and
wherein the tensioning spring mechanism is operatively connected to the proximal section of the filament such that the tensioning spring mechanism and the filament are moveable together without an actuation of the electroconductive filament and without bowing the distal end of the flexible elongate shaft.

16. The sphincterotome of claim 15, wherein the tensioning spring mechanism is configured such that it compensates between the tension in the filament and the compression in the shaft so as to reduce one of a premature bowing of the shaft and a slackness of the filament.

17. A sphincterotome having a proximal end and a distal end, and comprising:
a first handle portion comprising a connection to an elongate shaft; and
a second handle portion mounted to the first handle portion in a manner allowing proximal and distal sliding movement of the second handle portion relative to the first handle portion;
the second handle portion comprising
a connection to a filament; and
a generally longitudinally disposed tensioning spring mechanism configured for compensating a generally longitudinal tension of the filament, the tensioning spring mechanism connected to the filament such that the tensioning spring mechanism and the filament are moveable together in a manner not actuating the filament and thereby bowing a distal shaft end near a distal filament connection to the distal shaft end when the first and second handle portions are in an at-rest position;

wherein, during a first stage of movement out of the at-rest position, the movement of the second handle portion relative to the first handle portion equals a first distance, and the movement of the filament relative to the shaft equals a second distance, the first distance being greater than that second distance; and wherein during a second stage of movement out of the at-rest position, the movement of the second handle portion relative to the first handle portion equals a third distance, and the movement of the filament relative to the shaft equals a fourth distance, the third distance being substantially equal to the fourth distance, and the movement of the first and second handles is translated to the distal filament connection in a manner that at least partially bows the distal shaft end.

18. The sphincterotome of claim 17, wherein the tensioning spring mechanism comprises a coil spring connected between the second handle portion and the filament; and wherein during first stage of movement, the spring is not fully compressed, and during the second stage of movement, the spring is fully compressed.

19. The sphincterotome of claim 17, wherein the tensioning spring mechanism comprises a coil spring at least partially enclosed within a spring cover;

wherein during the first stage of movement, the spring cover is spaced away from an engagement surface of the second handle portion, and during the second stage of movement, the spring cover contacts the engagement surface of the second handle portion.

20. A sphincterotome comprising:

a tubular shaft having a shaft length, a proximal end portion and a distal end portion;

a filament having a filament length, a proximal end portion and a distal end portion, the distal end portion of the filament being affixed to the distal end portion of the shaft;

a first handle component comprising an attachment to the proximal end portion of the filament;

a second handle component reciprocally attached to the first handle component, the second handle component comprising a generally longitudinal attachment to the shaft; and configured such that at least one of the attachment of the first handle component to the filament and the attachment of the second handle component to the shaft is generally longitudinally adjustable without bowing the distal end portion of the shaft when the first and second handle components are in an at-rest position, wherein the filament is not actuated.

21. The sphincterotome of claim 20, wherein the shaft comprises a material that dimensionally alters as a result of a post-assembly process, and wherein the at least one of the attachment of the first handle component to the filament and the attachment of the second handle component to the shaft is adjustable to compensate for a change in the shaft length as result of the post-assembly process.

22. The sphincterotome of claim 21, further comprising having been subjected during at least a portion of the post-assembly process to at least one of heating, sterilization, and curing of at least a portion of the sphincterotome.

23. The sphincterotome of claim 20, wherein the at least one of the attachment of the first handle component to the filament and the attachment of the second handle component to the shaft is adjustable to compensate for a change in one of the shaft length and the filament length.

* * * * *